United States Patent [19]

Doran et al.

[11] Patent Number: 5,384,314

[45] Date of Patent: Jan. 24, 1995

[54] 1α-FLUORO-25-HYDROXY-16-ENE-23-YNE-CHOLECALCIFEROL

[75] Inventors: Thomas I. Doran, West Orange; Shian-Jan Shiuey, Nutley; Milan R. Uskokovic, Upper Montclair, all of N.J.

[73] Assignee: Hoffmann-La Roche Inc., Nutley, N.J.

[21] Appl. No.: 212,453

[22] Filed: Mar. 11, 1994

[51] Int. Cl.⁶ ............................................ C07C 401/00
[52] U.S. Cl. .................................... 514/167; 552/653
[58] Field of Search ......................... 552/653; 514/167

[56] References Cited

U.S. PATENT DOCUMENTS

| | | | |
|---|---|---|---|
| 5,087,619 | 2/1992 | Baggiolini et al. | 514/167 |
| 5,145,846 | 9/1992 | Baggiolini et al. | 514/167 |
| 5,190,935 | 3/1993 | Binderup et al. | 514/167 |
| 5,292,727 | 3/1994 | Godtfredsen | 514/168 |

OTHER PUBLICATIONS

Shiuey et al., J. Org. Chem. 55:243-247 (1990).
Kiegel et al., Tetrahedron Letters 32:6057-6060 (1991).

*Primary Examiner*—Johann Richter
*Assistant Examiner*—Kimberly J. Kestler
*Attorney, Agent, or Firm*—George M. Gould; George W. Johnston; Robert A. Silverman

[57] ABSTRACT

This invention is for 1α-fluoro-25-hydroxy-16-ene-23-yne-cholecalciferol, which can be further characterized by the formula:

and which is useful as an agent for the treatment of sebaceous gland diseases such as acne and sebhorreic dermatitis.

13 Claims, No Drawings

1α-FLUORO-25-HYDROXY-16-ENE-23-YNE-CHOLECALCIFEROL

BRIEF SUMMARY OF THE INVENTION

The invention relates to the compound 1α-fluoro-25-hydroxy-16-ene-23-yne-cholecalciferol, which can be further characterized by the formula:

and which is useful as an agent for the treatment of sebaceous gland diseases, such as acne or seborrheic dermatitis.

In still another aspect, the invention relates to pharmaceutical compositions comprising the compound of formula I and methods of using the compound of formula I.

DETAILED DESCRIPTION OF THE INVENTION

The invention relates to 1α-fluoro-25-hydroxy-16-ene-23-yne-cholecalciferol. 1α-fluoro-25-hydroxy-16-ene-23-yne-cholecalciferol can be prepared by the following reaction Scheme

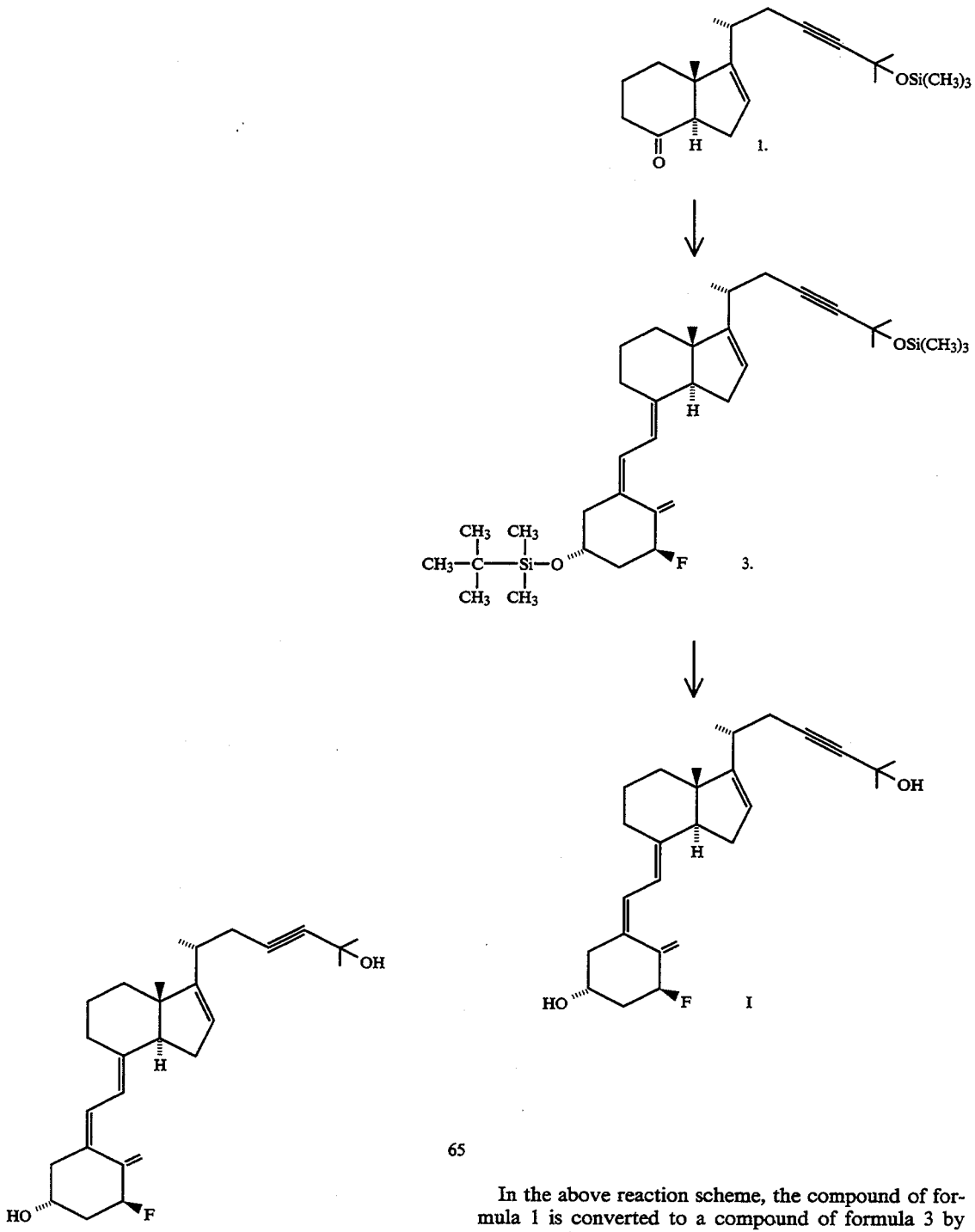

In the above reaction scheme, the compound of formula 1 is converted to a compound of formula 3 by reaction with a corresponding compound of formula:

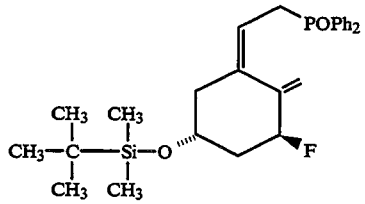

The reaction is carried out at −60° C.-90° C., preferably −75° C., in a polar, aprotic organic solvent, such as dry ether or more preferably dry tetrahydrofuran, in the presence of a strong base such as an alkyllithium like butyl lithium. The compound of formula 2 is known (J. Org. Chem. 1990, 55, 243) or can be prepared in accordance with known methods.

The protecting groups of a compound of formula 3 is removed by reaction with a fluorine salt, such as tetrabutyl-ammonium fluoride in a polar, organic solvent such as ether, or more preferably tetrahydrofuran, to yield a corresponding compound of formula I.

1α-fluoro-25-hydroxy-16-ene-23-yne-cholecalciferol is useful as an agent for the treatment of sebaceous gland diseases such as acne or seborrheic dermatitis.

1α-fluoro-25-hydroxy-16-ene-23-yne-cholecalciferol can be administered topically, for the treatment of sebaceous gland diseases such as acne or sebhorreic dermatitis, to hosts which need such treatment. More specifically, 1α-fluoro-25-hydroxy-16-ene-23-yne-cholecalciferol can be administered topically to a human in dosages that are in the range of 0.01 to 100 μg per gram of topical formulation per day for the treatment of sebaceous gland diseases such as acne or sebhorreic dermatitis.

1α-fluoro-25-hydroxy-16-ene-23-yne-cholecalciferol can be administered orally, for the treatment of sebaceous gland diseases such as acne or sebhorreic dermatitis to hosts which need such treatment. More specifically, 1α-fluoro-25-hydroxy-16-ene-23-yne-cholecalciferol can be administered orally in dosages that are in the range of about 0.01 to 10 μg per day for the treatment of sebaceous gland diseases such as acne or seborrheic dermatitis.

The useful activity of 1α-fluoro-25-hydroxy-16-ene-23-yne-cholecalciferol as an agent for the treatment of sebaceous gland diseases such as acne or sebhorreic dermatitis can be demonstrated by the following test procedures which are known in the art.

METHODS

1. In Vitro

Sebaceous cells were isolated from adult human sebaceous glands as in J. Invest. Dermatol. 96:341-348 (1991) and cultured on a layer of growth-arrested 3T3 mouse fibroblasts.

The cells were cultured in Iscove's medium containing 10% fetal calf serum and 4 μg/ml dexamethasone.

Cells were plated in medium without 1α-fluoro-25-hydroxy-16-ene-23-yne-cholecalciferol. 24–48 hours after the initial plating, the cultures were given fresh medium containing the compound of the invention. Every 48 hours, the cultures were given fresh medium containing the compound of the invention. On the day of harvesting, the cultures were rinsed with a 0.03% EDTA in PBS, to remove only the 3T3 fibroblasts. The remaining sebocyyte colonies were incubated in 0.05% trypsin/0.03% EDTA to create a single cell suspension of sebocytes. The cells were diluted, mixed vigorously to maintain a single cell suspension, and counted in a hemocytometer.

The compounds tested were handled in the following manner. Stock solutions were made up as $10^{-2}$M solutions in degassed 100% ethanol and stored at −20° C. in the dark. Solutions were never used after storage of more than one month. During experimental use the solutions, which were aliquoted, were thawed once and used by diluting directly into complete medium to the appropriate concentration, at $10^{-6}$, $10^{-7}$, $10^{-8}$M and $10^{-9}$. The compounds tested were (1) 1,25-dihydroxycholecalciferol; and (2) 1α-fluoro-25-hydroxy-16-ene-23-yne-cholecalciferol.

RESULTS

The compounds were tested for the inhibition of proliferation of sebaceous cells in vitro at the following concentrations: $10^{-6}$, $10^{-7}$, $10^{-8}$ and $10^{-9}$M. 1,25-dihydroxycholecalciferol is an agent reducing the size of sebaceous glands in ears of the male Syrian hamster.

The results are summarized in table 1 as the amount of compound necessary to inhibit the proliferation of the sebaceous cells by 50% as compared to a control ($ED_{50}$). The control was a culture treated with diluent only.

TABLE 1

| INHIBITION OF HUMAN SEBOCYTE PROLIFERATION IN VITRO | |
|---|---|
| Compound | $ED_{50}$ (μM) |
| 1,25-dihydroxycholecalciferol | 0.05 |
| 1α-fluoro-25-hydroxy-16-ene-23-yne cholecalciferol | 0.001 |

The results demonstrate that the inventive compound inhibits human sebocyte proliferation in vitro. Therefore, the inventive compound is useful as an agent for the treatment of acne.

2. In Vivo Hamster Ear Model a. Topical Study

The compound was evaluated for topical anti-acne activity in the hamster ear sebaceous gland model. For these studies, the compound was dissolved in acetone. Fifty (50) μl of the drug-containing solution was applied daily (5 days per week) to the dorsal side of the right ear of the hamster. Control hamsters received 50 μl of acetone. The animals were sacrificed after 4 weeks. The ears were removed and processed for histological evaluation. The ventral surface was separated from the rest of the ear. A 2 mm punch was removed 5 mm from the tip of the ear and stained in 0.1% Sudan Black B dissolved in 100% propylene glycol overnight. After destaining, the areas of the sebaceous glands were determined from the cross sections by image analysis using a Donsato Image Analysis System. The data was expressed as a percentage change from control animals for 80-120 sebaceous glands per dose. The results are summarized in table 2.

TABLE 2

| EFFECT OF 4 WEEKS TOPICAL DOSING ON HAMSTER FOR SEBACEOUS GLAND SIZE | | |
|---|---|---|
| Compound | Dose μg/animal | Change in Hamster Ear Sebaceous Gland Size Cross Section Analysis |
| 1α-fluoro-25-hydroxy- | 0.001 | −3 ns |

TABLE 2-continued

EFFECT OF 4 WEEKS TOPICAL DOSING ON HAMSTER FOR SEBACEOUS GLAND SIZE

| Compound | Dose μg/animal | Change in Hamster Ear Sebaceous Gland Size Cross Section Analysis |
|---|---|---|
| 16-ene-23-yne-cholecalciferol | 0.01 | −18 ns |
| | 0.1 | −28 ns |
| | 1.0 | −40 | ns = not statistically significant from controls b. Oral Study

The purpose of the test was to evaluate the effect of the inventive compound on the sebaceous glands of the hamster ear after oral administration of the compound. 200 μl of the compound of the invention dissolved in Tween 20/water/ethanol (50/40/100/0) administered daily (5 days per week) by garage to male Golden Syrian hamsters. The animals were sacrificed at 4 weeks and the ears were processed for histological evaluation. One ear was fixed with 10% buffered formalin, processed for paraffin embedding, sectioned, and stained with hematoxyline and eosin (H&E). The area of the sebaceous glands was measured on histologically prepared cross-sections of the ear by image analysis using a Leitz TAS Plus system. The data obtained from this study is presented below. Data is given as the average areas of 48 sebaceous glands per dose.

TABLE 3

EFFECT OF 4 WEEKS ORAL DOSING ON HAMSTER FOR SEBACEOUS GLAND SIZE

| Compound | Dose μg/kg | % Change in Hamster Ear Sebaceous Gland Size Cross Section Analysis |
|---|---|---|
| 1α-fluoro-25-hydroxy-16-ene-23-yne-cholecalciferol | 0.05 | −28 |
| | 0.5 | −28 |
| | 5.0 | −34 |
| | 50.0 | −35 |

The above data demonstrates that the inventive compound is useful as an agent in the treatment of sebaceous gland diseases such as acne or sebhorrheic dermatitis.

Oral dosage forms comprising 1α-fluoro-25-hydroxy-16-ene-23-yne-cholecalciferol may be incorporated in capsules, tablets and the like with pharmaceutically acceptable carrier materials.

Illustrative of the pharmaceutically acceptable carrier materials which may be incorporated into capsules, and the like are the following: a binder such as gum traganth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising 1α-fluoro-25-hydroxy-16-ene-23-yne-cholecalciferol include: ointments and creams encompassing formulations having oleaginous, absorbable, water-soluble and emulsion-type bases such as petrolatum, lanolin, polyethylene glycols and the like.

Lotions are liquid preparations and vary from simple solutions to aqueous or hydroalcohol preparations containing finely divided substances. Lotions can contain suspending or dispersing agents, for example, cellulose derivatives such as ethyl cellulose, methyl cellulose, and the .like; gelatin or gums, which incorporate the active ingredient in a vehicle made up water, alcohol, glycerin and the like.

Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as polyethylenecocoamine.

As used herein, the term "topical" denotes the use of the active ingredient, incorporated in a suitable pharmaceutical carrier, and applied at the site of the inflammation for the exertion of local action. Accordingly, the topical compositions include those pharmaceutical forms in which the compound is applied externally by direct contact with the skin. The topical dosage forms comprise gels, creams, lotions, ointments, powders, aerosols and other conventional forms for applying medication to the skin obtained by admixing a compound of formula I with known pharmaceutical topical carrier materials. In addition to application to the skin, the topical compositions of this invention can also be employed in the treatment of inflammations of mucous membranes, where such membranes are accessible to topical application of medication. For example, the topical composition can be applied to the mucous lining of the mouth or lower colon.

EXAMPLE 1

(1α,3β,5Z,7E)-1-fluoro-3[[(1,1-dimethyl-ethyl)dimethylsilyl]oxy]-25-[(trimethylsilyl)oxy]-9,10-secocholesta-5,7,10(19),16-tetraen-23-yne To a solution of 217 mg (0.461 mmol) of [3S-(1Z,3α,5β]-[2-[3-fluoro-5-[[(1,1-dimethylethyl)dimethylsilyl]oxy]-2-methylenecyclohexylidiene]ethyl]diphenylphosphine oxide in 6 mL of dry tetrahydrofuran was added dropwise at −75° C., 0.27 mL (0.43 mmol). of a 1.6M solution of n-butyl lithium in hexane. After the mixture was stirred for 6 minutes, a solution of 120 mg (0.346 mmol) of [1(R*),3aR*-3aβ, 7aα)]-3,3a,5,6,7,7a-hexahydro-1-(1,5-dimethyl-5-[(trimethylsilyl)oxy]-3-hexynyl)-7a-methyl-4H-indene-4-one in 5 mL of dry tetrahydrofuran was added dropwise. The mixture was stirred at −75° C. for 1,50 hours and quenched by addition of 1:1 mixture of 1M aqueous potassium sodium tartrate and 2M aqueous potassium bicarbonate. The mixture was extracted with ethyl acetate, and the organic phase was washed with brine, dried ($Na_2SO_4$), filtered, and evaporated to dryness. The residue was purified by column chromatography on silica gel using ethyl acetate-hexane (1:15) to give 136 mg (66%) of (1α,3β,5Z,7E)-1-fluoro-3[[(1,1-dimethyl-ethyl)dimethylsilyl]oxy]-25-[(trimethylsilyl)oxy]-9,10-secocholesta-5,7,10(19),16-tetraen-23-yne as a glass: IR (CHCl$_3$) 2230, 840 cm$^{-1}$; $^1$H NMR (CDCl$_3$) δ0.08 (s, 6H), 0.17 (s, 9H), 0.72 (s, 3H), 0.88 (s, 9H), 1.13 (d, J=8 Hz, 3H), 1.44 (s, 6H), 2.51 (m, 1H), 282 (m, 1H), 4.17 (br s, 1H), 5.11 (s, 1 H), 5.12 (dm, J=48 Hz, 1 H), 5.37 (s, 2H), 6.10 (d, J=12 Hz, 1 H), 6.34 (d, J=12 Hz, 1 H) mass spectrum, m/e 578 (M$^+$-HF).

EXAMPLE 2

1α-fluoro-25-hydroxy-16-ene-23-yne-cholecalciferol

To a solution of 132 mg (0.220 mmol) of (1α,3β,5Z,7E)-1-fluoro-3[[(1,1-dimethyl-ethyl)dimethylsilyl]oxy]-25-[(trimethylsilyl)oxy]-9,10-secocholesta-5,7,10(19),16-tetraen-23-yne in 8 mL of dry tetrahydrofuran was added 1.38 mL (1.38 mmol) of 1M tetrabutylammonium fluoride in tetrahydrofuran. The mixture was stirred at room temperature for 16 hrs. After dilution with water, the mixture was extracted with ethyl acetate. The organic phase was washed with water, brine, dried ($Na_2SO_4$) and evaporated to dryness. The residue was purified by column chromatography on silica gel using ethyl acetate-hexane (1:1:3) as the effluent to afford 81 mg (89%) of 1α-fluoro-25-hydroxy-16-ene-23-yne-cholecalciferol as a glass: $[\alpha]^{20} + 74.7$ (C 0.15, MeOH): IR ($CHCl_3$) 3600, 2230, 1649 $cm^{-1}$:$UV_{max}$ (EtOH) 242, 267 nm:$^1$H NMR ($CDCl_3$) δ0.72 (s, 3 H), 1.13 (d, J=8Hz, 3H), 1.48 (s, 6H) 2.63 (m, 1H), 283 (m, 1H), 4.24 (br s, 1H), 5.12 (s, 1H), 5.14 (dm, J=48 Hz, 1 H), 5.38 (s, 1 H), 5.40 (s, 1H), 6.12 (d, J=12 Hz, 1H), 6.41 (d, J=12 Hz, 1H); mass spectrum m/e 392 (M+-HF).

EXAMPLE 3

Oral Dosage Form Soft Gelatin Capsule

|  | mg/capsule |
|---|---|
| 1α-fluoro-25-hydroxy-16-ene-23-yne-cholecalciferol | 0.00001–0.010 |
| Butylated Hydroxytoluene (BHT) | 0.016 |
| Butylated Hydroxyanisole (BHA) | 0.016 |
| Myglyol ®-812 qs | 160 |

1. Suspend BHT and BHA in Myglyol ®-812. Warm to about 50° C., and stir until dissolved.
2. Dissolve 1α-fluoro-25-hydroxy-16-ene-23-yne-cholecalciferol in the solution from Step 1.
3. Fill the solution from Step 2 in a soft gelatin cap.

All steps are performed under a nitrogen atmosphere and protected from light.

|  | mg/capsule |
|---|---|
| 1α-fluoro-25-hydroxy-16-ene-23-yne-cholecalciferol | 0.00001–0.010 |
| BHT | 0.016 |
| BHA | 0.016 |
| Polyethylene Glycol 400 qs | 160 |

1. Suspend BHT and BHA in Polyethylene Glycol 400. Warm to about 50° C., and stir until dissolved.
2. Dissolve 1α-fluoro-25-hydroxy- 16-ene-23-yne-cholecalciferol in the solution from Step 1.
3. Fill the solution from Step 2 in a soft gelatin cap.

All steps are performed under a nitrogen atmosphere and protected from light.

EXAMPLE 5

Oral Dosage form Soft Gelatin Capsule

|  | mg/capsule |
|---|---|
| 1α-fluoro-25-hydroxy-16-ene-23-yne-cholecalciferol | 0.00001–0.010 |
| α-Tocopherol | 0.016 |
| Myglyol ®-812 qs | 160 |

1. Suspend α-Tocopherol in Myglyol ®-812. Warm to about 50° C., and stir until dissolved.
2. Dissolve 1α-fluoro-25-hydroxy-16-ene-23-yne-cholecalciferol in the solution from Step 1.
3. Fill the solution from Step 2 in a soft gelatin cap.

All steps are performed under a nitrogen atmosphere and protected from light.

EXAMPLE 6

Oral Dosage form Soft Gelatin Capsule

|  | mg/capsule |
|---|---|
| 1α-fluoro-25-hydroxy-16-ene-23-yne-cholecalciferol | 0.00001–0.010 |
| α-Tocopherol | 0.016 |
| Polyethylene Glycol 400 qs | 160 |

1. Suspend α-Tocopherol in Polyethylene Glycol 400. Warm to about 50° C., and stir until dissolved.
2. Dissolve 1α-fluoro-25-hydroxy-16-ene-23-yne-cholecalciferol in the solution from Step 1.
3. Fill the solution from Step 2 in a soft gelatin cap.

All steps are performed under a nitrogen atmosphere and protected from light.

It is claimed:

1. The compound, 1α-fluoro-25-hydroxy-16-ene-23-yne-cholecalciferol.

2. A pharmaceutical composition comprising an effective amount of 1α-fluoro-25-hydroxy-16-ene-23-yne-cholecalciferol and a carrier material.

3. A composition in accordance with claim 2 suitable for oral administration.

4. A composition in accordance with claim 3 wherein the amount of 1α-fluoro-25-hydroxy-16-ene-24-oxo-cholecalciferol is from about 0.01 to about 10 μg.

5. A composition in accordance with claim 2 suitable for topical administration.

6. A composition in accordance with claim 5 wherein the amount of 1α-fluoro-25-hydroxy-16-ene-23-yne-cholecalciferol is from about 0.01 to about 100 μg of topical formulation.

7. A method for treating sebaceous gland diseases which comprises administering to a host in need of such treatment an effective amount of 1α-fluoro-25-hydroxy-16-ene-23-yne-cholecalciferol.

8. A method of claim 7, wherein 1α-fluoro-25-hydroxy-16-ene-23-yne-cholecalciferol is administered orally.

9. A method in accordance with claim 8, wherein 1α-fluoro-25-hydroxy-16-ene-23-yne-cholecalciferol is administered in amounts of from about 0.01 to about 10 μg per day.

10. A method of claim 7, wherein 1α-fluoro-25-hydroxy-16-ene-23-yne-cholecalciferol is administered topically.

11. A method of claim 10, wherein 1α-fluoro-25-hydroxy-16-ene-23-yne-cholecalciferol is administered in an amount of from about 0.01 to about 100 μg per gram of topical formulation.

12. A method of claim 7, wherein the sebaceous gland disease is acne.

13. A method of claim 7, by wherein the sebaceous gland disease is sebhorreic dermatitis.

* * * * *

REEXAMINATION CERTIFICATE (3292nd)

United States Patent [19]
Doran et al.

[11] B1 5,384,314
[45] Certificate Issued Aug. 5, 1997

[54] 1α-FLUORO-25-HYDROXY-16-ENE-23-YNE-CHOLECALCIFEROL

[75] Inventors: Thomas I. Doran, West Orange; Shian-Jan Shiuey, Nutley; Milan R. Uskokovic, Upper Montclair, all of N.J.

[73] Assignee: Hoffmann-La Roche, Inc., Nutley, N.J.

Reexamination Request:
No. 90/004,133, Jan. 31, 1996

Reexamination Certificate for:
Patent No.: 5,384,314
Issued: Jan. 24, 1995
Appl. No.: 212,453
Filed: Mar. 11, 1994

[51] Int. Cl.⁶ .................. A61K 31/59; C07C 401/00
[52] U.S. Cl. ............................. 514/167; 552/653
[58] Field of Search ........................ 552/653; 514/167

[56] References Cited

U.S. PATENT DOCUMENTS

| | | | |
|---|---|---|---|
| 5,087,619 | 2/1992 | Baggiolini et al. | 514/167 |
| 5,145,846 | 9/1992 | Baggiolini et al. | 514/167 |
| 5,428,029 | 6/1995 | Doran et al. | 514/167 |
| 5,451,574 | 9/1995 | Baggiolini et al. | 514/167 |
| 5,512,554 | 4/1996 | Baggiolini et al. | 514/167 |

FOREIGN PATENT DOCUMENTS

| | | | |
|---|---|---|---|
| 2096105 | 11/1993 | Canada | C07C 401/00 |

OTHER PUBLICATIONS

Ferrara, et al, Journal of Biol. Chem., vol. 269(4), pp. 2971–2981, Jan. 28, 1994.
Zhou, et al, Blood, vol. 78(1), pp. 75–82, Jul. 1, 1991.
Endocrinology vol. 129(4) pp. 1876–1884 (1991).
Cancer Research, vol. 50, pp. 6857–6864 (Nov. 1, 1990).
Proc. Workshop—Vitamin D pp. 433–434 1988–7th.

*Primary Examiner*—Shailendra Kumar

[57] ABSTRACT

This invention is for 1α-fluoro-25-hydroxy-16-ene-23-yne-cholecalciferol, which can be further characterized by the formula:

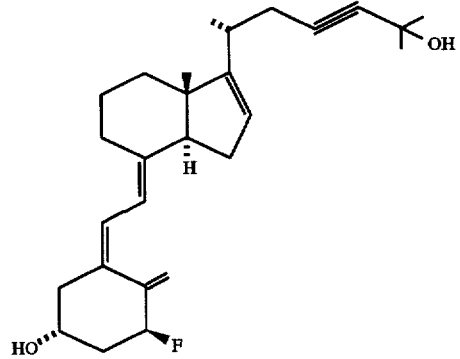

and which is useful as an agent for the treatment of sebaceous gland diseases such as acne and sebhorreic dermatitis.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 7–13 is confirmed.

Claims 1–6 are cancelled.

* * * * *